United States Patent von Bebenburg et al.

[11] 3,969,361
[45] July 13, 1976

[54] 2-BENZOYL-3-AMINO-PYRIDINES

[75] Inventors: Walter von Bebenburg, Buchschlag; Heribert Offermanns, Grossauheim, both of Germany

[73] Assignee: Deutsche Gold- und Silber-Scheideanstalt vormals Roessler, Germany

[22] Filed: Aug. 15, 1974

[21] Appl. No.: 497,750

Related U.S. Application Data

[63] Continuation-in-part of Ser. No. 347,361, April 3, 1973, Pat. No. 3,875,176.

[30] Foreign Application Priority Data

May 10, 1972  Austria .............................. 4113/72

[52] U.S. Cl. .................... 260/295 AM; 260/296 R; 260/294.8 E; 260/297 R; 260/294.9; 424/263; 424/295 CA; 260/45.8 W
[51] Int. Cl.² ...................................... C07D 213/75
[58] Field of Search.............................. 260/295 AM

[56] References Cited
UNITED STATES PATENTS 3,555,035  1/1971  Meisels et al................. 260/295 AM

*Primary Examiner*—Natalie Trousof
*Assistant Examiner*—Robert T. Bond
*Attorney, Agent, or Firm*—Cushman, Darby & Cushman

[57] ABSTRACT

There are prepared compounds of the formula

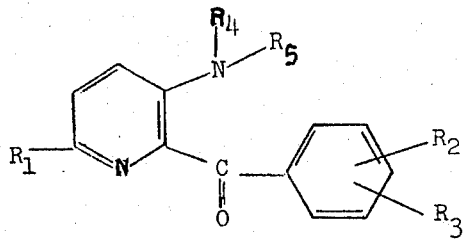

where $R_1$ is halogen, $R_2$ and $R_3$ are hydrogen, halogen, trifluoromethyl, hydroxy, cyano, lower alkyl or lower alkoxy, $R_4$ is hydrogen or lower alkyl, and $R_5$ is hydrogen, lower alkyl, benzoyl, substituted benzoyl, lower carbalkoxy or

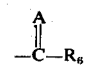

where A is oxygen, sulfur, imino or lower alkylimino and $R_6$ is lower alkyl, lower alkyl having 1 to 3 halogen atoms, lower alkenyl, hydroxymethyl, carboxymethyl, carb-lower alkoxy methyl, amino lower alkyl or alkylaminoalkyl having 2 to 13 carbon atoms or where any hydroxy or primary or secondary amino group is substituted by an alkanoyl group of 2 to 8 carbon atoms, carbalkoxy having 1 to 6 carbon atoms, carbophenoxy or carbobenzyloxy or a pharmacologically acceptable salt thereof. The compounds are useful in emotional disturbances, tension, anxiety, increased irritability.

11 Claims, No Drawings

2-BENZOYL-3-AMINO-PYRIDINES

This application is a continuation-in-part of application Ser. No. 347,361 filed Apr. 3, 1973 now U.S. Pat No. 3,875,176. The entire disclosure of the parent application is hereby incorporated by reference.

The invention is directed to the product of compounds of the formula

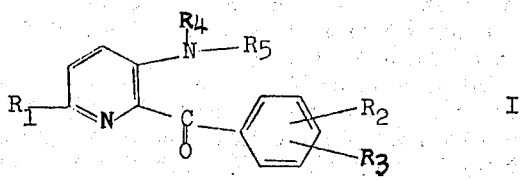

where $R_1$ is halogen, e.g. chlorine, bromine or fluorine, $R_2$ and $R_3$ are hydrogen, e.g. fluorine, chlorine or bromine, trifluoromethyl, hydroxy, cyano, lower alkyl, e.g. of 1 to 6 carbon atoms or lower alkoxy, e.g. of 1 to 6 carbon atoms, $R_4$ is hydrogen or lower alkyl, e.g. 1 to 6 carbon atoms and $R_5$ is hydrogen, lower alkyl, e.g. 1 to 6 carbon atoms, benzoyl, substituted benzoyl, lower carbalkoxy, e.g. with 1 to 6 carbon atoms or

where A is oxygen, sulfur, imino or lower alkylimino, e.g. with 1 to 7 carbon atoms and $R_6$ is lower alkyl, e.g. of 1 to 7 carbon atoms, lower alkyl having 1 to 3 halogen atoms, e.g. alkyl of 1 to 7 carbon atoms wherein the halogens are chlorine, bromine or fluorine, lower alkenyl, e.g. with 2 to 7 carbon atoms, hydroxymethyl, carboxymethyl, carb-lower alkoxy methyl, e.g. with 1 to 7 carbon atoms, amino lower alkyl, e.g. with 1 to 7 carbon atoms, or alkylaminoalkyl having 2 to 13 carbon atoms or where any hydroxy or primary or secondary amino group is substituted by an alkanoyl group of 2 to 8 carbon atoms, carbalkoxy having 1 to 6 carbon atoms, carbophenoxy or carbobenzyloxy or a pharmacologically accepted salt thereof.

As halogens there are employed chlorine, fluorine and bromine, i.e. halogens of atomic weight 9 to 80, especially chlorine and bromine. In the above named lower alkyl, alkenyl, alkylamino, alkoxy, alkylimino, alkanoyl and carbalkoxy groups preferably there are present 1 to 6 carbon atoms (2 to 6 carbon atoms for the alkenyl group), especially 1 to 4 carbon atoms (2 to 4 carbon atoms for the alkenyl group). (This is also true if these groups are present in the compound with a further chemical redical designation such as for example, carbalkoxymethyl and aminoalkyl). These groups, especially the alkyl and alkenyl groups can be straight or branched chain. The substituted benzoyl group ($R_5$) is substituted in the phenyl nucleus with one to three (o, m or p- positions) halogen atoms, especially chlorine, bromine or fluorine and/or lower alkyl, e.g. with 1 to 6 carbon atoms, especially 1 to 4 carbon atoms (for example methyl). Preferably, the substituents are in the o- and p- positions. The halogen substituted alkyl groups can have 2 or 3 halogen atoms, for example, fluorine atoms or the same carbon atoms as is the case for example with the trifluoroacetyl group.

An especially preferred group of compounds within formula I is that wherein $R_1$ is chlorine, $R_2$ is hydrogen or halogen, $R_3$ is hydrogen, $R_4$ is hydrogen or alkyl with 1 to 3 carbon atoms and $R_5$ is hydrogen or an aliphatic acyl group of 2 to 4 carbon atoms or an aliphatically unsaturated acyl group with 3 to 5 carbon atoms, (e.g. ethylenically unsaturated), a haloacetyl group, an aminoacetyl group, a carbmethoxy group, a carbethoxy group or a benzoyl group.

Even more preferred are compounds of formula I where $R_1$ is chlorine, $R_2$ is hydrogen, chlorine or fluorine, $R_3$ is hydrogen, $R_4$ is hydrogen or methyl, $R_5$ is hydrogen, acetyl, propionyl, chloroacetyl, bromoacetyl or aminoacetyl.

In addition to the compounds mentioned in the specific working examples, there can also be made by the same procedures other compounds within the invention such as 2-benzoyl-3-amino-6-fluoropyridine, 2-benzoyl-3-amino-6-bromo-pyridine, 2-benzoyl -3-(3,3-dimethyl-acryloxylamino)-6-bromopyridine, 2-benzoyl-3-benzoylamino-6-fluoro-pyridine, 2-(p-chlorobenzoyl)-3-amino-6-chloro-pyridine, 2-(m-chlorobenzoyl)-3-amino-6-chloropyridine, 2-(o-bromobenzoyl)-3-amino-6-chloropyridine, 2-(p-bromobenzoyl) -3-amino-6-bromo-pyridine, 2-(o-fluorobenzoyl)-3-amino-6-fluoropyridine, 2-(o-chlorobenzoyl)-3-methylamino)-6-chloro-pyridine, 2-benzoyl-3-chloroacetylamino-6-chloro-pyridine, 2-benzoyl-3-bromoacetyl-amino-6-chloro-pyridine, 2-benzoyl-3-ethylamino-6-chloropyridine, 2-(o-chlorobenzoyl)-3-isopropylamino-6-chloropyridine, 2-benzoyl-3-n-propylamino-6-bromopyridine, 2-benzoyl -3-butyrylamino-6-chloropyridine, 2-benzoyl-3-acryloylamino-6-chloropyridine, 2-benzoyl-3-(methacryloyl ethylamino)-6-chloropyridine, 2-benzoyl-3-carbmethoxyamino-6-chloro-pyridine, 2-benzoyl-3-carbethoxy-methylamino, -6-chloropyridine, 2-(o-trifluoromethyl-benzoyl)-3-amino-6-chloro-pyridine, 2-(o-methylbenzoyl)-3-amino-6-chloro-pyridine, 2-(p-ethylbenzoyl)-3-amino-6-chloropyridine, 2-(2',4'-dimethylbenzoyl)-3-amino-6-bromopyridine, 2-(2'-chloro-4-methyl-benzoyl)-3-amino-6-chloropyridine, 2-(o-butylbenzoyl)-3-amino-6-chloropyridine, 2-(p-hexylbenzoyl)-3-amino-6-chloropyridine, 2-(o-hydroxybenzoyl)-3-amino-6-chloropyridine, 2-(p-hydroxybenzoyl)-3-acetylamino-6-chloropyridine, 2-(2',4'-dihydroxybenzoyl)-3-amino-6-chloropyridine, 2-(o-cyanobenzoyl)-3-amino-6-chloropyridine, 2-(m-cyanobenzoyl)-3-methylamino-6-chloropyridine, 2-benzoyl-3-trifluoroacetylamino-6-chloropyridine, 2-benzoyl-3-carbophenoxyamino-6-chloropyridine, 2-benzoyl-3-carboamyloxy-6-chloropyridine, 2-benzoyl-3-(beta-chloropropionyl-amino-6-chloropyridine, 2-benzoyl-3-dihexylamino-6-chloropyridine, 2-benzoyl-3-thiopropionylamino-6-chloropyridine, 2-benzoyl-3-thiocarbethoxy-amino-6-chloropyridine, 2-(o-chlorobenzoyl)-3-thiobenzoylamino-6-chloropyridine, 2-(p-chlorobenzoyl)-3-thioacetamino-6-chloropyridine, 2-(o-chlorobenzoyl)-3-benzyloxythiocarbonylaminoacetamino-6-chloropyridine, 2-benzoyl-3-(2-chloro-acryloylamino)-6-chloropyridine, 2-benzoyl -3-ethyliminoamino-6-chloropyridine, 2-benzoyl-3- propyl(methyl) iminoamino-6-chloropyridine, 2-benzoyl-3-iminocarbethoxyamino -6-chloropyridine, 2-(o-methoxybenzoyl)-3-amino-6-chloropyridine, 2-(p-ethoxybenzoyl)-3-methylamino-6-chloropyridine.

There can be prepared and used the salts with pharmacologically acceptable acids such as hydrochloric acid, hydrobromic acid, succinic acid, tartaric acid, fumaric acid, sulfuric acid, citric acid, phosphoric acid, lactic acid, malonic acid, maleic acid, acetic acid, propionic acid and p-toluenesulfonic acid.

The compounds of the invention have valuable pharmacodynamic properties. Especially they have marked sedative, psychosedative and anxiolytic properties as well as antiphlogistic properties.

The new compounds can be prepared by methods which are known in themselves.

The methods of preparing the compounds include a. Reacting a compound of formula I where $R_4$ is hydrogen and $R_5$ is hydrogen or a lower alkyl group with a compound of the formula

II where A and $R_6$ are as defined above and E is a halogen, especially chlorine or bromine, a hydroxy group or an acylated hydroxy or reacting with aliphatic lactones containing 3–8 carbon atoms, or b. In a compound of the general formula I converting the compound where $R_4$ and/or $R_5$ are as defined above or $R_5$ is also another acyl group as is customarily used in peptide chemistry is converted to another compound of formula I by alkylation, acylation, saponification, catalytic hydrogenation or reaction with phosphorus pentasulfide or ammonia or a lower monoalkylamine having 1–6 carbon atoms, or c. in compounds of formula III

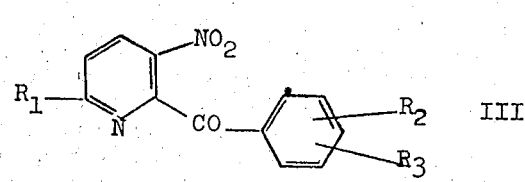
III wherein $R_1$, $R_2$ and $R_3$ are as defined above reducing the nitro group to an amino group and in a given case alkylating the amino group formed with a lower alkyl group and/or with a compound of formula II or acylating with an aliphatic lactone of 3 to 8 carbon atoms.

Process (a)

Process (a) is suitably carried out in a solvent such as an aliphatic alcohol, e.g. methyl alcohol, ethyl alcohol, isopropyl alcohol or butyl alcohol, dioxane tetrahydrofurane, dimethyl sulfoxide or dimethyl formamide at a temperature between 0° and 150°C. The process can be carried out in the presence of basic materials such as pyridine, quinoline, triethylamino, diisopropylamine, potassium carbonate and sodium carbonate, etc. In case E is an acylated hydroxy group, especially preferred acyl groups are those derived from lower saturated aliphatic carboxylic acids having 2 to 6 carbon atoms, as, for example, the acetyl, hexanoyl and propionyl groups.

In the case where E is a hydroxy group the reaction is undertaken in the presence of known condensation agents such as dicyclohexylcarbodiimide, diimidazolylcarbonyl 1,2-dihydroquinoline or N-ethoxycarbonyl-2-ethoxy-1,2-dihydroquinoline.

If lactones are used the reaction takes place, for example, in inert organic solvents at temperatures between 20° – 250°C., in a given case with the use of conventional condensation agents. Preferably beta or gamma lactones are used.

Examples of suitable compounds within formula II are acetyl chloride, acetyl bromide, thioacetyl chloride, propionyl chloride, propionyl bromide, thiopropionyl bromide, hexanoyl chloride, thiohexanoyl chloride, butyryl chloride, octanoyl chloride, chloroacetyl chloride, chloropropionyl chloride, bromoacetyl chloride, acryloyl chloride, acryloyl bromide, 2-chloroacryloyl chloride, methacryloyl chloride, 3,3-dimethylacryloyl chloride, methyl chloroformate, ethyl chloroformate, hexyl chloroformate, benzoyl chloride, benzoyl bromide, acetic acid, propionic acid, hexanoic acid, aminoacetyl chloride, glycine beta-aminopropionic acid, omega-amino-hexanoic acid, omega-aminoctanoic acid.

Process (b)

One or two lower alkyl groups are introduced by alkylation into compounds of formula I in which both $R_4$ and $R_5$ are hydrogen or one of these groups is hydrogen. As alkylating agents there can be used, for example, esters of the formulae $R'_5$ Hal, $ArSO_2OR'_5$ and $SO_2(OR'_5)_2$ wherein Hal is a halogen atom (especially chlorine, bromine or iodine), $R'_5$ is an alkyl group of 1 to 6 carbon atoms and Ar is an aromatic group which, for example, can be a phenyl or naphthyl group which in a given case is substituted by one or more lower alkyl groups. Examples are methyl chloride, ethyl bromide, methyl iodide, ethyl chloride, propyl bromide, isopropyl chloride, butyl chloride, butyl bromide, butyl iodide, sec. butyl chloride, sec. butyl bromide, t-butyl chloride, sec. butyl bromide, t-butyl chloride, amyl chloride, hexyl chloride, heptyl chloride, methyl benzene sulfonate, ethyl benzene sulfonate, alkyl esters of p-toluene sulfonic acid such as methyl p-toluenesulfonate, ethyl p-toluenesulfonate, propyl p-toluene sulfonate, butyl p-toluene-sulfonate, isobutyl p-toluenesulfonate, hexyl p-toluenesulfonate, methyl 2,4-xylenesulfonate, methyl alpha naphthalenesulfonate, ethyl beta naphthalene sulfonate, lower dialkyl sulfates such as dimethyl sulfate, diethyl sulfate, dipropyl sulfate, dibutyl sulfate and the like. The alkylation can take place, in a given case with addition of customary acid binding agents such as bases, e.g. sodium hydroxide and potassium hydroxide, alkali carbonates such as sodium carbonate and potassium carbonate, alkali hydrides, e.g. sodium hydride, alkali amides, e.g. sodamine, alkali alcoholates, e.g. sodium methylate, potassium ethylate, sodium ethylate, sodium octylate, sodium decylate, pyridine or other conventional tertiary amines, e.g. dimethyl aniline, triethylamine, or tributyl amine at a temperatue between 0° and 150°C. in inert solvents such as alcohols, e.g. methyl alcohol, ethyl alcohol, propyl alcohol, isopropyl alcohol, butyl alcohol or amyl alcohol, dioxane, dimethyl formamide, dimethyl sulfoxide, aromatic hydrocarbons such as benzene, toluene or xylene or ketones such as acetone and methyl ethyl ketone (also see L. F. and Mary Fieser "Reagents for Organic Synthesis", John Wiley and Sons, Inc. New York, 1967, Vol. 1, pages 1303–4; Vol. 2, page 471 and Vol. 3 (1972) page 349.) The alkylation can also be carried out to introduce a lower alkyl group starting with a compound of formula I in which $R_4$ is hydrogen and $R_5$ is already present as the stated acyl group or as another easily splittable acyl group or, in a given case, a substituted benzyl group (the alkylation being suitably carried out as given above in the presence of a base or active alkali compound) and subsequently hydrolyzing off or hydrogenating off the $R_5$ group by known methods (for example as given below).

As easily splittable groups there can be used, for example, the benzyl group, α-phenylethyl group, benzyl groups substituted in the benzene nucleus as, for example, the p-bromo or p-nitrobenzyl group, the carbobenzoxy group, the carbobenzthio group, the trifluoroacetyl group, the phthalyl radical, the trityl radical, the p-toluenesulfonyl radical, the tert. butylcarboxy group and other protective groups used in the synthesis of peptides (see, for example Jesse P. Greenstein and Milton Winitz "Chemistry of Amino Acids", John Wiley and Sons, Inc. New York (1961) Vol. 2, pages 883 et seq.) The alkylation of the $R_4$ and $R_5$ containing amino group can also be carried out by reacting a compound of formula I where $R_4$ and $R_5$ are hydrogen and the remaining groups $R_1$, $R_2$ and $R_3$ are as defined above with an aliphatic aldehyde of 1 to 6 carbon atoms, e.g. formaldehyde, acetaldehyde, propionaldehyde, acrolein, butyraldehyde, valeraldehyde, capraldehyde, methacrolein or crotonaldehyde or an aliphatic ketone with 3 to 6 carbon atoms, e.g. acetone, methyl ethyl ketone, diethyl ketone, or methyl butyl ketone to form the corresponding Schiff's base and simultaneously or subsequently hydrogenating. These processes can be carried out at room temperature or elevated temperature in solvents such as aliphatic alcohols, e.g. methyl alcohol, ethyl alcohol, propyl alcohol, isopropyl alcohol or butyl alcohol, alcohol water-mixtures, e.g. 96% ethyl alcohol, dimethyl formamide, or dimethyl formamide containing mixtures, etc. For the hydrogenation there can be used, for example, the usual hydrogenation catalysts such as platinum, palladium or nickel with or without carriers.

In the case where $R_5$ is

A can be exchanged in various ways: Thus, in case A is oxygen, this atom can be replaced by a sulfur atom by means of phosphorus pentasulfide. This reaction takes place in inert solvents such as benzene, toluene, xylene, dioxane, pyridine, quinoline or chlorohydrocarbons, e.g. chlorobenzene at temperatures between 0° and 100°C. The thus obtained sulfur compound (thioamide), as well as the amides themselves can be reacted in a polar medium with lower alkyl amines having 1 to 6 carbon atoms, e.g. methyl amine, ethyl amine, isopropyl amine, butyl amine, amyl amine or hexyl amine or ammonia whereby compounds are formed of formula I in which the group A of the $R_5$ radical is an imino or lower alkylimino group. These reactions can be carried out in polar solvents such as methanol, ethanol, isopropanol or excess amine at temperatures between 0° and 150°C.

In case the radical $R_5$ is the group

wherein $R_6$ is a haloalkyl group, then this halogen atom can be exchanged for an amino or alkylamino group by reaction with ammonia or an aliphatic alkylamine having 1 to 6 carbon atoms in an organic solvent such as methanol, ethanol or dioxane at a temperature between 0° and 150°C. An excess of amino compound is favorable to the reaction.

If the radical $R_5$ signifies the group

wherein $R_6$ is an acylated amino group, this acyl group can be split off by selective saponification. There can be especially employed easily splittable acyl groups or in a given case substituted benzyl groups as are used in peptide chemistry such as those pointed out supra. This saponification can be carried out, for example, in water, methanol, ethanol, glacial acetic acid or mixtures of these or other solvents which contain the acid or base corresponding to that used for hydrolysis (e.g. potassium carbonate, sodium carbonate, alkali, e.g. sodium hydroxide or potassium hydroxide, ammonia, etc.). The temperature is between 20° and 150°C. Various acyl groups, as for example, the carbobenzoxy radical and the p-tolyloxycarbonyl radical also can be split off by catalytic hydrogenation in the presence of customary hydrogenation catalysts, especially palladium catalysts in a solvent or suspension agent, in a given case under elevated pressure. As solvents or suspension agents there can be used, for example, water, lower aliphatic alcohols, e.g. methyl alcohol, ethyl alcohol or isopropyl alcohol, cyclic ethers such as dioxane or tetrahydrofurane, aliphatic ethers, e.g. diethyl ether or dipropyl ether, dimethyl formamide, etc. as well as mixtures of these materials. For splitting off there can be used all the methods employed in peptide and aminoacid chemistry for the removal of protective groups, see the Greenstein et al book cited above. Hydroxy or amino groups which are present can be correspondingly acylated by the conditions given with process (a) or they can be alkylated as given above.

Process (c)

Process (c) is carried out suitably in a solvent such as methanol, ethanol, isopropanol, dioxane or tetrahydrofurane at temperatures between 0° and 150°C. The reduction can be carried out with hydrogen in the presence of metal catalysts such as Raney-nickel, Raney-cobalt or noble metal catalysts (palladium, platinum), in a given case on suitable carriers, et pressure of 1 to 100 atmosphere absolute.

If chemical reduction is employed there can be used nascent hydrogen with zinc, tin or iron and dilute acids, e.g. hydrochloric acid, aluminum amalgam/$H_2O$ or alkali hydrides or complex metal hydrides such as $LiAlH_4$, LiH, sodium triethoxy aluminum hydride, sodium dihydro bis(2-methoxyaluminate) and similar reducing agents or $H_2S$, ammonium sulfide or alkali sulfides, e.g. sodium sulfide or potassium sulfide.

For the further reaction according to process (c) the solution resulting from the reduction can be used directly without previous isolation of the amino compound.

Basic compounds of formula I can be converted into their salts by known methods. As anions for these salts there can be used any of the known and therapeutically usable acid radicals such as those set forth above for example.

If the compounds of formula I contain acid groups then these can be converted in conventional manner into their alkali (e.g. sodium or potassium), ammonium or substituted ammonium salts. As substituted ammonium salts there may be especially noted salts of tertiary alkyl amines, lower aminoalcohols and bis and tris (hydroxyalkyl) amines in which the alkyl radicals contain 1 to 6 carbon atoms such as triethylamine, ethanolamine, diethanolamine, triethanolamine, propanolamine, dipropanolamine, trimethylamine, diethyl propyl amine, tributylamine, trihexylamine.

The free bases can be prepared again from the salts of the compounds in the usual manner, for example, by treating a solution in an organic solvent such as an alcohol (e.g. methanol) with soda or sodium hydroxide or by means of a dilute acid (for example dilute acetic acid).

Those compounds of formula I which contain asymmetric carbon atoms and as a rule result as racemates, can be split into the optically active isomers in known manner with the help of an optically active acid. However, it is alos possible to employ from the beginning an optically active starting material whereby a correspondingly optically active or diastereomer form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, cremes, powders, liquids, dusts or aerosols. As liquids there can be used, for example, oily or aqueous solutions or suspensions, emulsions, injectable aqueous and oily solutions or suspensions.

Those starting materials for processes (a), (b) and (c) which are not known can be prepared in the following ways.

A compound of the formula

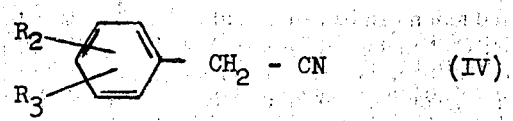

or

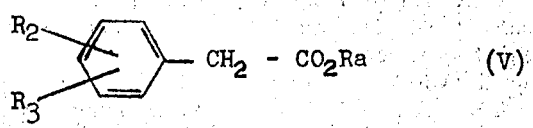

where Ra is hydrogen or lower alkyl. It is first reacted with an active alkali compound such as sodamide, potassium amide, sodium hydride or finely divided sodium in an inert solvent such as dimethyl formamide, dioxane or benzene and then there is chopped in with stirring and in a nitrogen atomsphere the calculated amount of 2,6-dichloro-3-nitropyridine dissolved in the same solvent. In many cases it has proven also suitable to change the sequence of addition, for example, to add the alkali compound to a solution of phenylacetic acid or benzyl cyanide derivative and 2,6-dichloro-3-nitropyridine. The generally exothermic reaction results in the alkali salt of a compound of formula VI.

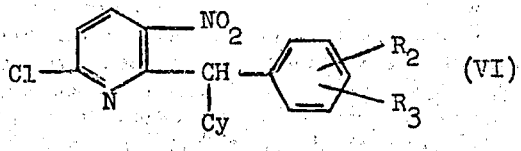

where cy is CN or $CO_2Ra$, which salt if colored strongly blue or violet. After the end of the reaction this is filtered off with suction, washed, dissolved in water and treated with diluted glacial acetic acid until disappearance of the intrinsic color. The compound of formula VI customarily crystallizes out in adequate purity.

As illustrative of this procedure 2-[alpha-cyano-)-o-chlorobenzyl]-3-nitro-6-chloropyridine was obtained as follows:

To a solution of 120 grams of o-chlorobenzylcyanide in 1.5 liters of dioxane with stirring and in a nitrogen atmosphere there were added at 45°C. 42 grams of sodium hydride (80% in white oil). Then the mixture was stirred for 45 minutes at this temperature. It was then cooled and at 20° to 22°C.; there were dropped in 140 grams of 2,6-dichloro-3-nitropyridine in 500 ml. of dioxane within 30 minutes. Reaction was allowed to continue for 3 hours at this temperature. The deeply colored sodium salt was filtered off with suction, washed with dioxane, dissolved in water/methanol (1:1 by volume) and dilute acetic acid until change in color occurred. The desired compound crystallized out, was filtered off with suction and washed thoroughly with methanol. M.P. 174° to 175°C; Yield 91 grams.

From the compounds of formula VI the corresponding 2-benzoyl-3-nitro-6-chloropyridine derivations of formula VII

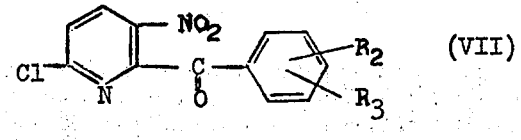

can be obtained by oxidation. This can be accomplished, for example, with selenium dioxide in dioxane or tetrahydrofurane at 50° to 150°C. or it can also be accomplished with 30% hydrogen peroxide solution at temperatures below 100°C., preferably 20° to 50°C. in acetone-water wherein the stoichrometrical amount of an aqueous concentrated KOH solution is dropped in just quick enough that no color disappearance takes place. In the last procedure the chlorine atom in the 6 position to a large extent is simultaneously hydrolytically split off. Therefore there is isolated not only the desired compound but also a compound analogous to that of formula VII where R₁ is OH. The latter can be again chlorinated in known manner with a mixing or PCl₃/PCl₅, whereby the PCl₃ again deoxygenates the N-oxide simultaneously formed as byproduct.

The nitro group in the compounds of formula VII is then reduced to the amino group either catalytically (with Pd, Pt, or Raney nickel in alcohols, e.g. methyl alcohol, ethyl alcohol or isopropyl alcohol, dioxane or tetrahydrofurane at 0° to 60°C; an at 1 to 50 atmospheres absolute) or chemically (with LiAlH₄ or Al/Hg/H₂O, for example, in diethyl ether, dioxane or tetrahydrofurane between 0° to 100°C). This amino group can then be alkylated with an alkyl group of 1 to 6 carbon atoms in the manner described previously.

Compounds of formula VIII

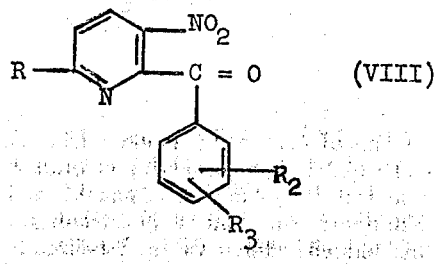

where R₁ is F or Br and can be prepared, for example, by heating a compound of formula VII with a saturated aqueous alcoholic ammonia solution in an autoclave at 100° to 1200°C. for several hours (2 to 4 hours) and then in known manner diazotizing the 6-amino-pyridine formed and reacting under the conditions of the Sandmeyer reaction or modified Sandmeyer reaction in the presence of fluoride or bromide ions and/or the corresponding copper (I) salts (Cu, Br, CuCl) or heating with fluoborate ions. As solvents there can be used water-alcohol mixture or mixtures of water, dimethyl formamide and dimethyl sulfoxide. For the production of fluoro derivative the dry diazomine fluoborate can also be decomposed thermally.

Compounds of formula VIII in which R₁ signifies a bromine atom can also be prepared by brominating compounds of formula VIII in which R₁ is OH by use of a brominating agent such as POBr₃, PBr₃ or SOBr₂, in a given case in an inert solvent, between 20° and 200°C. The production of compounds of formula VIII in which R₁ is F can also take place in a modified manner in which there is gradually added NaNO₂ to a solution of a compound of formula VIII where R₁ signifies amino in concentrated aqueous hydrofluoric acid at a temperature between 0° and 50°C., or else a slow stream of nitrous gases is led into such a solution.

The reduction of the nitro group as well as, in a given case, the subsequent introduction of R₅ can take place in the manner already described.

For example, there are prepared compounds of formula I where R₁ is chlorine, bromine or fluorine, R₂ and R₃ are in the o and/or p-position, where R₂ is chlorine, bromine, fluorine, the trifluoromethyl group, the hydroxy group, the methyl group or the methoxy group and R₃ is hydrogen or a radical which is one of those indicated for R₂, R₄ is hydrogen or an alkyl group of 1 to 6 carbon atoms, especially 1 to 3 carbon atoms and R₅ is hydrogen or an alkanoyl group with 2 to 8 carbon atoms, especially 2 to 4 carbon atoms, or an alkanoyl group of 2 to 8 carbon atoms, especially 2 to 4 carbon atoms, which is substituted with 1 to 3 halogen atoms, especially fluorine or chlorine, preferably in the alpha position (for example a haloacetyl group such as trifluoroacetyl or fluoroacetyl) or an alkanoyl group of 2 to 8 carbon atoms, especially 2 to 4 carbon atoms, substituted with an amino group, or a straight or branched chain alkanoyl group of 3 to 8 carbon atoms, especially 3 to 6 carbon atoms, or a carbalkoxy group of 2 to 8 carbon atoms, especially 2 to 5 carbon atoms (for example, the carbethoxy group, the carbamyloxy group, the carboctoxy group) or the benzoyl group or a benzoyl group substituted with halogen atoms or methyl groups; in case R₅ is an alkanoyl group substituted by the amino group or alkylamino group, the amino group is preferably present in the alpha position (for example the aminoacetyl group) wherein a hydrogen atom of this amino group can also be substituted by the carbophenoxy radical, the carbobenzyloxy radical a carbalkoxy radical of 3 to 4 carbon atoms, especially 3 carbon atoms or by an alkanoyl radical of 2 to 4 carbon atoms (for example the acetyl radical or the propionyl radical).

Unless otherwise indicated all parts and percentages are by weight.

EXAMPLE 1

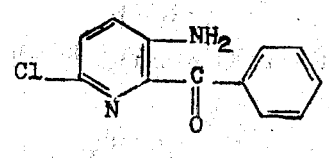

75 grams of 2-benzoyl-3-nitro-6-chloropyridine in 500 ml of dioxane were hydrogenated with 20 grams of Raney nickel at 50 atmospheres absolute and 30° to 50°C. The filtered hydrogenated solution was evaporated in a vacuum and the residue recrystallized once from ethanol. Yield 52 grams. M.P. 160°C.

The starting material of example 1 was prepared in the following manner.

To a cooled and stirred solution of 190 grams of 2,6-dichloro-3-nitro-pyridine and 117 grams of benzyl cyanide in 2 liters of dioxane there was added gradually in a nitrogen atmosphere 64 grams of sodium hydride (80% in white oil). The reaction mixture immediately became colored a deep dark blue, gradually a fine particled precipitate began to separate out, the temperature increased (with cooling with ice water) to 30°C. After 3 hours there were added about 20 ml of ethyl alcohol, stirring continuously for 20 minutes and then the mixture filtered with suction. The deep blue sodium salt was dissolved in 1 liter of water and then treated with dilute acetic acid until the color disappeared. The 2-(alpha-cyanobenzyl)-3-nitro-6-chloropyridine crystallized out in pure form. M.P. 165°C.; Yield 146 grams.

A mixture of 200 grams of 2-(alpha-cyanobenzyl)-3-nitro-6-chloropyridine, 5–0 ml of acetone and 160 ml of 30% aqueous hydrogen peroxide solution with stirring were treated dropwise at 35° – 40°C. with a concentrated potassium hydroxide solution (made of 75 grams of KOH and 50 ml of water). The dropwise addition took place just quick enough that a disappearance of color did not take place. Immediately after a disappearance of color remained, which indicated the end of the reaction, the mixture was cooled and the crystalline material which separated was filtered off with suction. This material, the amount of which varies between 30 and 40 grams, in 2-benzoyl-3-nitro-6-chloropyridine which can be purified through recrystallization from methanol. M.P. 106°C. The filtrate was acidified with dilute hydrochloric acid, whereupon 2-benzoyl-3-nitro-6-hydroxy-pyridine precipitated out in an amount between 120 and 140 grams, M.P. 211°C.

This hydroxy compound was likewise converted into the desired 2-benzoyl-3-nitro-6-chloropyridine by chlorination. For this purpose 190 grams of 2-benzoyl-3-nitro-6-hydroxypyridine was stirred in a mixture of 200 ml of phosphorus trichloride, 500 ml. of phosphorus oxychloride and 190 grams of phosphorus pentachloride for 4 hours at 72°C. Then the phosphorus halides were distilled off in a rotary evaporator in a vacuum, the residue taken up in 1 liter of chloroform and washed with ice water, twice with dilute sodium hydroxide and twice with water. The chloroform solution was dried, brought to dryness in a vacuum and the residue recrystallized from methanol. Yield 145 grams; M.P. 106°C.

EXAMPLE 2

2-(o-chlorobenzoyl)-3-amino-6-chloropyridine

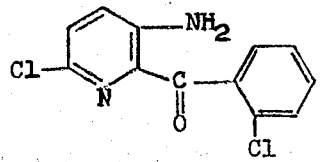

79 grams of 2-o-chlorobenzoyl)-3-nitro-6-chloropyridine were hydrogenated in 500 ml of dioxane with 20 grams of Raney nickel at 50 atmospheres absolute at 30° to 50°C., the filtered hydrogenated solution was evaporated in a vacuum and residue recrystallized once from ethanol. Yield 55 grams; M.P. 170°C.

The starting material was made in a manner analogous to that employed in example 1 but starting from o-chlorobenzyl cyanide.

EXAMPLE 3

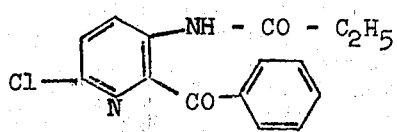

43 grams of 2-benzoyl-3-amino-6-chloropyridine were dissolved in 100 ml of dioxane, then 16 ml of pyridine and finally with stirring 18 ml of propionyl chloride were added. The mixture was stirred for 2 hours, then water was added until crystallization began. The material which precipitated was recrystallized from methanol/water. Yield 48 grams; M.P. 140°C.

EXAMPLE 4

2-benzoyl-3-(3,3-dimethyl-acryloylamino)-6-chloropyridine

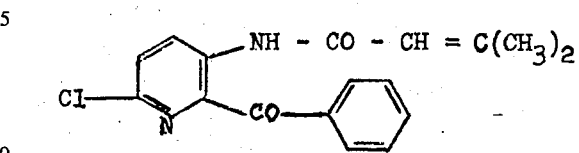

grams of 2-benzoyl-3-amino-6chloropyridine and 14 grams of 3,3-dimethyl acrylcyl chloride were stirred for 2 hours in 100 ml of dioxane and 9.5 ml of pyridine and then treated with water unitl crystallization began. The precipitated material was recrystallized from methanol-water. Yield 23 grams; M.P. 168°C.

EXAMPLE 5

2-benzoyl-3-carbethoxyamino-6-chloropyridine

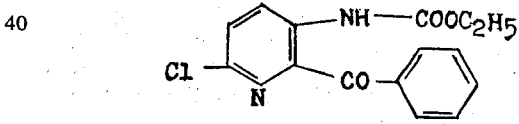

30 grams of 2-benzoyl-3-amino-6-chloropyridine and 20 grams of ethyl chloroformate were stirred for 2 hours in 100 ml of dioxane and 20 ml of pyridine and then treated with water until crystallization began. The precipitated material was recrystallized from methanol-water. Yield 32 grams; M.P. 98°C.

EXAMPLE 6

2-benzoyl-3-benzeylamino-6-chloropyridine

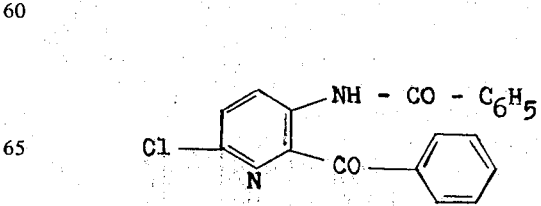

11.5 grams of 2-benzoyl-3-amino-6-chloropyridine and 7 grams of benzoyl chloride were stirred for 2 hours in 100 ml of dioxane and 16 ml of pyridine and then treated with water until crystallization began. The precipitated material was recrystallized from methanol-water. Yield 11 grams; M.P. 146° to 147°C.

EXAMPLE 7

2-benzoyl-3-benzyloxycarbonylaminoacetamino-6-chloropyridine

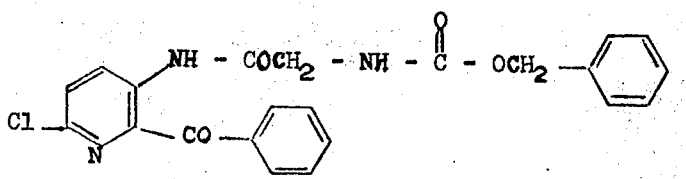

21 grams of N-benzyloxycarbonyl glycine were suspended in 400 ml of ether and 21 grams phosphorus pentachloride added with stirring. A clear solution formed. After 30 minutes there were added a solution of 23 grams of 2benzoyl-3-amino-6-chloropyridine in 90 ml of chloroform whereupon a weak exothermic reaction occurred. The mixture was stirred for 2 hours at room temperature, the precipitate which crystallized out was filtered off with suction and subsequently washed with ether. Yield 30 grams; M.P. 130°C.

EXAMPLE 8

2-benzoyl-3-aminoacetamino-6-chloropyridine

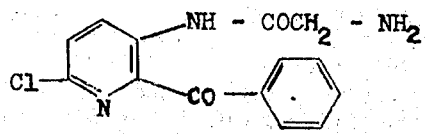

29 grams of 2-benzoyl-3-benzyloxycarbonylaminoacetamino-6-chloropyridine were added in portions to 120 ml of a 30% solution of HBr in 99% glacial acetic acid at −5° to 0°C. The portions went into solution with strong development of $CO_2$. After 15 minutes about 50 ml of dry ether were added. The precipitated material was filtered off with suction after 30 minutes and washed with ether. Yield 50 grams; M.P. of the hydrobromide 250°C.

EXAMPLE 9

2-benzoyl-3-(propionyl-methylamino)-6-chloropyridine

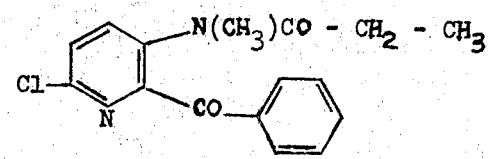

47 grams of 2-benzoyl-3-propionylamino-6-chloropyridine (prepared as in example 3) were dissolved in 200 ml of dimethyl formamide; with stirring and in a nitrogen atmosphere there were added 5.5 grams of 80% sodium hydride in white oil; after 30 minutes there were dropped in 29 ml of methyl iodide and the mixture stirred for 2 hours at 50°C. Then there were added 10 ml of methanol and the mixture evaporated in a vacuum. The compound came out as an oil.

EXAMPLE 10

2benzoyl-3-methylamino-6-chloropyridine

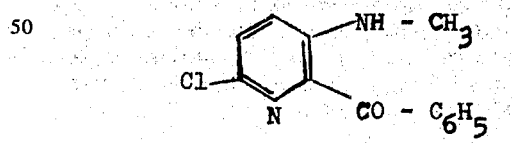

50 grams of 2-benzoyl-3-(propionyl-methylamino)-6-chloropyridine were taken up in 100 ml of ethanol. 200 ml of water and 200 ml of concentrated hydrochloric acid were added. The mixture was heated at reflux for 10 hours and then treated with 1 liter of water. The syrup which precipitated crystallized after rubbing for some time. The material was recrystallized from ethanol. Yield 24 grams; M.P. 77°C.

EXAMPLE 11

2-(o-chlorobenzoyl)-3-acetamino-6-chloropyridine

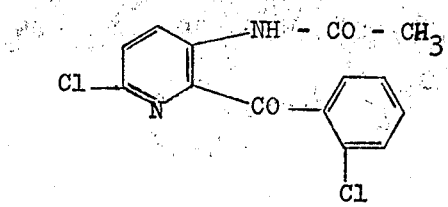

70 grams of 2(o-chlorobenzoyl)-3-amino-6-chloropyridine in 500 ml of dioxane were treated with 26 ml of pyridine and 73 ml of acetyl chloride and stirred for 1 hour. Water was added until turbidity occurred, whereupon the reaction product crystallized out and this was recrystallized from ethanol. Yield 63 grams; M.P. 132°C.

EXAMPLE 12

2-(o-chlorobenzoyl)-3-benzyloxycarbonyl-aminoacetamino-6-chloropyridine

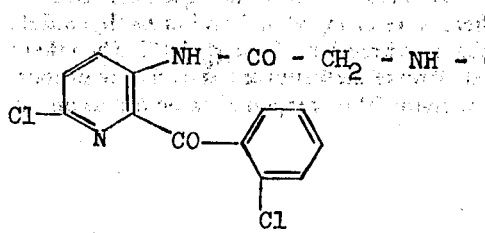

27 grams of benzyloxycarbonyl glycine were suspended in 200 ml of dry dioxane and 27 grams of $PCl_5$ added. To this solution there were added 34 grams of 2-(o-chlorbenzoyl)-3amino-6-chloropyridine and stirred for another hour. Subsequently the mixture was treated with petroleum ether until there was complete precipitation of the reaction product. Yield 50 grams; M.P. 105°C.

EXAMPLE 13

2-(o-chlorobenzoyl)-3-aminoacetamino-6-chloropyridine

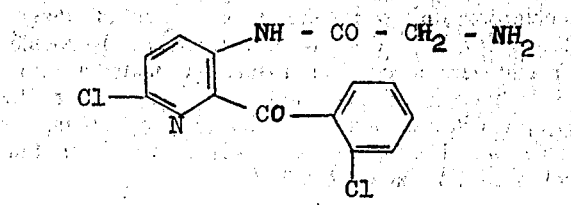

50 grams of 2-(o-chlorobenzoyl)-3-benzyloxycarbonylaminoacetamino-6-chloropyridine were added portionwise at 0°C. to 100 ml of 99% acetic acid saturated with HBr whereupon a strong development of $CO_2$ occurred. After 1 hour of stirring the mixture was treated with ether until turbidity developed. Yield 35 grams; the hydrobromide melted at 210°C. (decomposition).

EXAMPLE 14

2-(o-fluorobenzoyl)-3-amino-6-chloropyridine

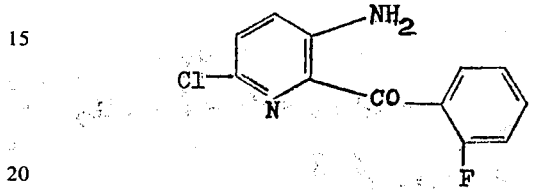

49 grams of 2-(o-fluorobenzoyl)-3-nitro-6-chloropyridine were hydrogenated in 500 ml of dioxane with addition of 10 grams of Raney nickel at a hydrogen pressure of 40 atmospheres absolute and a temperature of 40° to 60°C. The filtered hydrogenated solution was concentrated in a vacuum to about 100 ml whereupon the reaction product crystallized out. It was recrystallized from ethanol. Yield 36 grams; M.P. 180° to 181°C.

The starting material was made in a manner analogous to that employed in example 1 but starting from o-fluorobenzyl cyanide.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical carriers and diluents, as well as other customary carriers and assistants.

Such carriers and assistants are set forth, for example, in Ullmann's Encyklopädie der technischer Chemie, Vol. 4 (1953), pages 1 to 39; Journal of Pharmaceutical Sciences, Vol. 52 (1963), pages 918 et seq; H. v. Czetsch-Lindenwald, Hilfstoffe für Pharmazie und angrenzende Gebiete; as well as in Pharm. 2nd Vol. 2 (1961) pages 72 et seq.; Dr. H. P. Fiedler, Lexicon der Hilfstoffe für Pharmazie, Kosmetik und angrenzende Gebiete, Cantor Kg.Aulendorf i. Wurtt, 1971.

Examples of such materials include gelatin, natural sugars such as sucrose or lactose, lecithin, pectin, starch (for example corn starch), tylose, talc, lycopodium, silica (for example coloidal silica), cellulose derivatives (for example, cellulose ethers in which the cellulose hydroxy groups partially or completely are etherified with lower alkyl alcohols and/or hydroxyalkyl alcohols, e.g. methyl cellulose, ethyl cellulose, hydroxyethyl cellulose, hydroxypropyl cellulose, or methyl hydroxyethyl cellulose), micropulverized cellulose, stearates, e.g. methylstearate, and glyceryl stearate, magnesium and calcium salts of fatty acids of 12-22 carbon atoms, e.g. calcium stearate, emulsifiers, fats, oils, especially plantoils (for example peanut oil, castor oil, olive oil, sesame oil, cotton seed oil, corn oil, mono-, di- and triglycerides of saturated fatty acids having 12 to 18 carbon atoms and their mixtures, e.g. glycerol tristearate, glycerol tripalmitate, glycerol trilaurate, glycerol distearate, glycerol monostearate, pharmaceutically compatible mono- and polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, as well as derivatives of such alcohols and polyglycols, dimethyl sulfoxide, esters of saturated and unsaturated fatty acids (2 to 22 carbon atoms, especially 10 to 18 carbon atoms) with monovalent alcohols (1 to 20 carbon atoms) such as ethyl alcohol, methyl alcohol, octadecyl alcohol, eicosanyl alcohol or polyhydric alcohols such as glycols, glycerine, diethylene glycol, pentaerythritol sorbitol, mannitol, etc., e.g. glycerol stearate, glyceryl palmitate, pentaerythritol stearate, ethylene glycol stearate; such esters of polyvalent alcohols can in a given case also be etherified, benzyl benzoate, dioxolane, glycerine formal, glycol furfural, dimethyl acetamide, lactamide, lactates, e.g., ethyl lactate, ethyl carbonate, silicones (especially medium viscosity dimethyl polysiloxane) etc.

For production of solutions there can be used, for example, water or physiologically compatible organic solvents as, for example, ethanol, 1,2-propylene glycol, polyglycols, e.g. triethylene glycol, and their derivatives, dimethyl sulfoxide fatty alcohols, e.g. lauryl alcohol, octadecyl alcohol and oleyl alcohol, triglycerides, partial esters of glycerine, paraffins, etc.

For the production of the preparations there can be used the conventional solvent aids. As solvent aids there can be used, for example, polyoxyethylated fats, polyoxyethylated oleotriglycerides, linoleized oleotriglycerides. Examples of oleotriglycerides are olive oil, peanut oil, castor oil, sesame seed oil, cotton seed oil, corn oil (see also Dr. H. P. Fiedler "Lexikon der Hilfstoffe fur Pharmazie," Kosmetik and angrenzende Gebiete 1971, pages 191 to 195). By the term polyoxyethylated is meant those materials where the polyoxyethylene chain contains 2 to 40, and especially 10 to 20, ethylene oxide units. Such polyoxyethylated materials can be obtained, for example, by reacting the corresponding glyceride with ethylene oxide (for example 40 moles of ethylene oxide per mole of glyceride).

Furthermore there can be added preservatives, stabilizers, buffers, taste correctives, antioxidants and complex formers (for example ethylenediaminotetraacetic acid) and the like. In a given case for stabilization of the active molecule a pH range of about 3–7 can be established with physiologically compatible acids or buffers. Generally a neutral to weakly acid (to pH 5) pH value is preferred.

As antioxidants there can be used, for example, sodium meta bisulfite, ascorbic acid, gallic acid, alkyl gallates, e.g. methyl gallate, ethyl gallate and propyl gallate, butylated hydroxyanisole, nordihydroguaiaretic acid, tocopherol (alphatocopherol) as well as tocopherol and synergists (as for example lecithin, ascorbic acid or phosphoric acid). The addition of the synergist considerably increases the antioxidant activity of tocopherol.

As preservatives there can be used, for example, sorbic acid, p-hydroxybenzoic acid esters (for example lower alkyl esters such as methyl p-hydroxybenzoate and ethyl p-hydroxybenzoate), benzoic acid, sodium benzoate, trichloroisobutyl alcohol, phenol, cresol, benzethonium chloride and formatin derivatives.

The pharmacological and galenical treatment of the compounds of the invention takes place according to the usual standard methods. For example, the active material or materials and the assistant or carrier material are well mixed by homogenizing or stirring (for example by means of a colloid mill or ball mill). Temperatures between 20° and 80°C., preferably 20° to 50°C. are employed.

The drugs can be used orally, parenterally, rectally, vaginally, perlingerally or topically or as sprays, e.g. in aerosols.

The addition of other medicinally active materials is also possible or desirable.

The compounds of the invention in combat tests and carrageenin edema tests show good sedative, psychosedative, anxiolytic and antiphlogistic activity.

This activity is comparable with the activity of the known medicine Diazepam.

The lowest effective dosages in animal experiments, for example, are:

2 mg/kg body weight orally
1 mg/kg sublingually
0.5 mg/kg intravenously

As a general range of dosage for anxiolytic activity (based on animal studies) there can be employed:

2–100 mg/kg body weight orally
1–50 mg/kg sublingually
0.5–20 mg/kg intravenously The compounds of the invention have utility in treating irritation, tension, anxiety, increased irritability, psychoneurotic disturbances of children. Vegetative dystony, psychosomatic disturbances and organic neuroses. Sleep disturbances, muscular spasms (also in illnesses of the rheumatic cycle). Treatment of cramps.

For facilitating birth, abortus imminens, threatened or initiated early birth or miscarriage, placenta praevia. Preparation for operation.

The pharmaceutical preparations generally contain either 1 or 2 of the active components of the invention.

The compounds can be delivered in the form of tablets, capsules, pills, dragees, suppositories, gels, cremes, powders, liquids, dusts or aerosols. As liquids there can be used oily or aqueous solutions or suspensions or emulsions. The preferred forms of use are tablets which contain between 2 and 50 mg of active material or solutions which contain between 0.1 and 1% of active material.

In individual doses the amount of active component of the invention can be used, for example, in an amount of 2–10 mg dispensed orally or 0.5–5 mg dispensed parenterally (for example intravenously or intramuscularly).

When used rectally or vaginally there is employed between 1 and 10 mg.

There is no specific dosage for inhalation (as solution or aerosol) or for local application to the skin or mucous membrane (for example in the form of solutions, lotions, emulsions, salves, etc.)

The dosages set forth are always calculated as the free base.

For example, there is recommended the use of 1 to 2 tablets containing 2 to 10 mg of active ingredient 3 times daily or for intravenous injection 1 to 3 times a day a 1 to 2 ml ampoule containing 0.5 to 10 mg of active material is recommended. In oral application the minimum daily dosage is, for example, 2 mg., the maximum daily dosage should not be over 50 mg.

For the treatment of dogs and cats the individual oral dosage generally is between about 2 and 20 mg/kg of body weight; the parenteral dosage between approximately 0.5 and 1.0 mg/kg of body weight.

For the treatment of horses and cattle the oral dosage is generally between about 2 and 20 mg/kg; the parenteral individual dosage is between about 0.5 and 10 mg/kg of body weight.

The acute toxicity of the compounds of the invention in the mouse (expressed by the LD 50 mg/kg method of Miller and Tainter, Proc. Soc. Exph. Biol. and Med., Vol. 57 (1944) pages 251 et seq.) in oral application is between 500 and 3000 mg/kg (or above 500 mg/kg).

The drugs can be used in human medicine, in veterinary medicine, e.g., to treat cats, dogs, horses, sheep, cattle, goats and pigs or in agriculture. The drugs can be used alone or in admixture with other pharmacologically active materials.

The salts, e.g. the hydrochloride salts, are also useful as curing agents for melamine formaldehyde resins.

Additional examples of compounds which are within the present invention and having the uses set forth above are described below:

EXAMPLE 15

2-Benzoyl-3-chloracetamido-6-chloro-pyridine

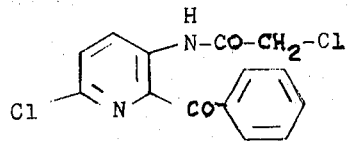

There were added 140 grams of 2-benzoyl-3-amino-6-chloropyridine in portions to a mixture of 55 ml of chloroacetyl chloride and 300 ml of dioxane. Then the mixture was stirred for an additional hour and there treated with 200 ml of ethanol and 400 ml of gasoline. Then it was filtered with suction and the substance recrystallized from alcohol. Yield: 140 grams; M.P. 140°–142°C.

EXAMPLE 16

2-Benzoyl-3-bromacetamido-6-chloropyridine

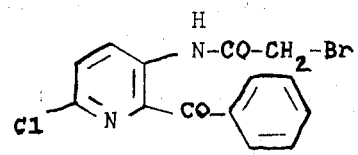

To a solution of 312 grams of 2-benzoyl-3-amino-6-chloropyridine in 1250 ml of acetone there were added dropwise in 15 minutes 135 ml. of bromacetyl chloride with ice cooling. After some time the reaction product crystallized out and it was filtered off with suction after 2 hours.

Yield: 363 grams; M.P. 128°C.

EXAMPLE 17

2-(o-Chlorobenzoyl-)-3-trifluoroacetylamino-6chloropyridine

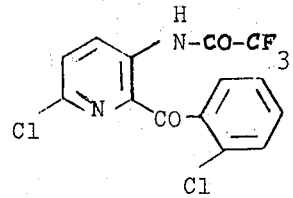

134 grams of 2-(o-chlorobenzoyl-) 3-amino-6-chloropyridine were suspended in 200 ml of chloroform and there were dropped in at 30°–35°C. with stirring trifluoroacetic anhydride. After 30 minutes of stirring the solution formed was evaporated to dryness and the residue recrystallized from ethanol. Yield: 147.5 grams; M.P. 148°C.

EXAMPLE 18

2-(o-Chlorobenzoyl-)-3-(p-chlorobenzoylamino-)-6-chloropyridine

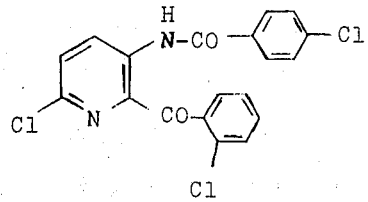

26.7 grams of 2-(o-chlorobenzoyl)-3-amino-6-chloropyridine were dissolved in 100 ml of dioxane with addition of 9 ml of pyridine. Then 19.3 grams of p-chlorobenzoyl chloride was added with stirring. After 2 hours the solution was filtered, treated with some water until crystallization and filtered with suction. The product was recrystallized from dioxane. Yield: 25 grams; M.P. 215°–217°C.

EXAMPLE 19

2-(o-Fluorobenzoyl)-3-(p-chlorobenzoylamino-)-6-chloropyridine

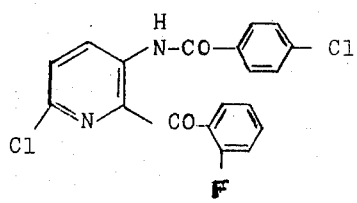

This compound was made in a manner analogous to example 18 starting from 26 grams of 2-(o-fluorobenzoyl)-3-amino-6-kchloropyridine.
Yield: 22 grams; M.P. 203°–205°C.

EXAMPLE 20

2-Benzoyl-3-(aminoacetamino-)-6-chloropyridine

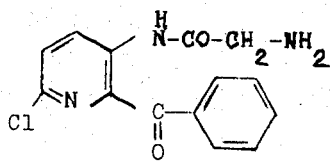

100 grams of 2-benzoyl-3-brom-acetamino-6-chloropyridine were introduced into 400 ml of liquid ammonia with stirring. The mixture was stirred at −40°C. for 4 hours. Then the ammonia was allowed to evaporate. The solid residue was dissolved in 400 ml of methylene chloride and the solution washed once with 400 ml of water. The organic phase was dried and treated with stirring with 400 ml of gasoline, whereby the washed product precipitated. Yield: 50 grams; M.P. 200°–201°C. The starting material was made in Example 16.

EXAMPLE 21

2-Benzoyl-3-(ethylamino-acetamido)-6-chloropyridine

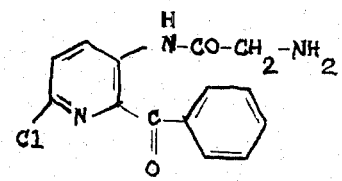

34.4 grams of 2-benzoyl-3-bromoacetamido-6-chloropyridine were introduced with stirring at room temperature into a mixture of 50 grams of ethylamine and 150 ml of methanol. After temporarily dropping, the temperature increased to 30°C. after stirring for one hour the substance which crystallized out was filtered with suction, dissolved in dioxane and treated with 6 normal ethanolic hydrogen chloride solution. The precipitated salt was filtered off with suction and washed with dioxane. Yield: 23.8 grams; M.P. 196°–200°C. (for the hydrochloride)

What is claimed is:

1. A pyridine compound of the formula

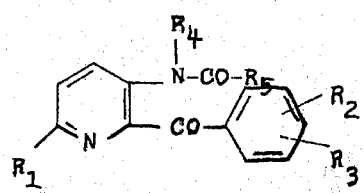

where $R_1$ is halogen, $R_2$ is hydrogen, halogen, trifluoromethyl, hydroxy, lower alkyl or lower alkoxy, $R_3$ is hydrogen, halogen, hydroxy or lower alkyl, $R_4$ is hydrogen or lower alkyl and $R_5$ is phenyl or halophenyl or a pharmacologically acceptable acid addition salt thereof.

2. A compound according to claim 1 wherein all halogen atoms in the compound have an atomic weight of 9 to 80.

3. A compound according to claim 1 wherein $R_2$ is hydrogen, halogen, trifluoromethyl of an alkyl group with 1 to 4 carbon atoms, $R_3$ is hydrogen, halogen or alkyl of 1 to 4 carbon atoms, $R_4$ is hydrogen or alkyl of 1 to 4 carbon atoms.

4. A compound according to claim 3 wherein $R_1$ is chlorine or bromine.

5. A compound according to claim 4 wherein $R_1$ is chlorine.

6. A compound according to claim 1 wherein $R_2$ is hydrogen or halogen, $R_3$ is hydrogen and $R_4$ is hydrogen or methyl.

7. A compound according to claim 1 which is 2-benzoyl-3-benzoylamino-6-chloropyridine.

8. A compound according to claim 1 which is 2-(o-chlorobenzoyl)-3-(p-chlorobenzoylamino)-6-chloropyridine.

9. A compound according to claim 1 which is 2-(o-fluorobenzoyl)-3-(p-chlorobenzoyl-amino)-6-chloropyridine.

10. A compound according to claim 1 wherein all halogen atoms in the compound have an atomic weight of 9 to 80, $R_2$ is hydrogen, halogen, trifluoromethyl or an alkyl group with 1 to 4 carbon atoms, $R_3$ is hydrogen, halogen or alkyl of 1 to 4 carbon atoms and $R_4$ is hydrogen or alkyl of 1 to 4 carbon atoms.

11. A compound according to claim 10 wherein $R_4$ is hydrogen.

* * * * *